(12) United States Patent
Banister et al.

(10) Patent No.: US 6,946,580 B2
(45) Date of Patent: Sep. 20, 2005

(54) HYDROFORMYLATION PROCESS WITH RECYCLE OF ACTIVE RHODIUM CATALYST

(75) Inventors: James Andrew Banister, Durham (GB); George Edwin Harrison, Essex (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/479,309

(22) PCT Filed: May 29, 2002

(86) PCT No.: PCT/GB02/02510

§ 371 (c)(1),
(2), (4) Date: Apr. 30, 2004

(87) PCT Pub. No.: WO02/096848

PCT Pub. Date: Dec. 5, 2002

(65) Prior Publication Data

US 2004/0186323 A1 Sep. 23, 2004

(30) Foreign Application Priority Data

May 30, 2001 (GB) .............................................. 0113080

(51) Int. Cl.⁷ .............................................. C07C 45/50
(52) U.S. Cl. ...................................... 568/451; 568/454
(58) Field of Search ................................. 568/451, 454

(56) References Cited

U.S. PATENT DOCUMENTS

| | | |
|---|---|---|
| 3,527,809 A | 9/1970 | Pruett et al. |
| 3,755,393 A | 8/1973 | Kniese et al. |
| 4,113,754 A | 9/1978 | Kummer et al. |
| 4,388,279 A | 6/1983 | Quick |
| 4,482,749 A | 11/1984 | Dennis et al. |
| 4,496,768 A | 1/1985 | Dennis et al. |
| 4,496,769 A | 1/1985 | Dennis et al. |
| 5,208,194 A | 5/1993 | Pitchai et al. |
| 5,773,665 A | 6/1998 | Silverman et al. |

FOREIGN PATENT DOCUMENTS

| | | |
|---|---|---|
| GB | 1338237 | 11/1973 |
| GB | 1582010 | 12/1980 |
| WO | WO 97/03938 A1 | 2/1997 |

*Primary Examiner*—Johann Richter
*Assistant Examiner*—Sikarl A. Witherspoon
(74) *Attorney, Agent, or Firm*—Davidson, Davidson & Kappel, LLC

(57) ABSTRACT

The present invention relates to a continuous hydroformylation process for the production of an aldehyde by hydroformylation of an olefin which comprises: providing a hydroformylation zone containing a charge of a liquid reaction medium having dissolved therein a rhodium hydroformylation catalyst comprising rhodium in combination with carbon monoxide and a ligand; supplying the olefin to the hydroformylation zone; maintaining temperature and pressure conditions in the hydroformylation zone conducive to hydroformylation of the olefin; recovering from the liquid hydroformylation medium a hydroformylation product comprising aldehyde; recovering from the hydroformylation zone a stream comprising the rhodium catalyst; contacting at least a portion of the stream with a solid acidic absorbent under process conditions which allow at least some of the rhodium to become bound to the absorbent; subjecting the rhodium bound to the absorbent, under process conditions which allow desorption of the metal, to a fluid stripping medium comprising hydrogen and solvent; recovering the rhodium hydride catalyst; and recycling the rhodium hydride catalyst to the hydroformylation zone.

27 Claims, 8 Drawing Sheets

HYDROFORMYLATION PROCESS WITH RECYCLE OF ACTIVE RHODIUM CATALYST

FIELD OF THE INVENTION

The present invention relates to an improved hydroformylation process. In particular, it relates to a process for the hydroformylation of olefins to give aldehydes. Most particularly, it relates to a process for the hydroformylation of $C_2$ to $C_{20}$ olefins or higher in which process conditions may be used which have not been possible heretofore.

BACKGROUND OF THE INVENTION

Hydroformylation is a well known reaction in which an olefin, usually a terminal olefin, is reacted under suitable temperature and pressure conditions with hydrogen and carbon monoxide in the presence of a hydroformylation catalyst to give an aldehyde, or a mixture of aldehydes, having one more carbon atom than the starting olefin. Thus a hydroformylation reaction with propylene will yield a mixture of n- and iso-butyraldehydes, of which the straight chain n-isomer is usually the more commercially desirable material. The hydrogen and carbon monoxide will generally be supplied to the hydroformylation reactor as synthesis gas.

Examples of hydroformylation processes can be found in U.S. Pat. Nos. 4,482,749, 4,496,768 and 4,496,769 which are incorporated herein by reference.

The catalysts first used in hydroformylation reactions were cobalt-containing catalysts, such as cobalt octacarbonyl. However, the presence of these catalysts meant that the reactor had to be operated at exceptionally high pressures, e.g. several hundred bars, in order to maintain the catalysts in their active form.

Rhodium complex catalysts are now conventionally used in the hydroformylation of both internal olefins and alpha-olefins, that is to say compounds containing the group —CH=CH$_2$, —CH=CH—, >C=C<, >C=CH—, —CH=C< or >C=C$_2$H. One advantage of these catalysts is that lower operating pressures, e.g. to about 20 kg/cm$^2$ absolute (19.6 bar) or less, may be used than was usable with the cobalt catalysts. A further advantage noted for the rhodium catalysts was that they are capable of yielding high n-/iso-aldehyde product ratios from alpha-olefins; in many cases n-/iso-aldehyde molar ratios of 10:1 and higher can be achieved.

Further, since the rhodium catalyst is non-volatile, product recovery was greatly simplified. A fuller description of the process can be found in the article "Low-pressure OXO process yields a better product mix", Chemical Engineering, Dec. 5, 1977. Also relevant to this process are U.S. Pat. No. 3,527,809, GB-A-1338237 and GB-A-1582010 which are incorporated herein by reference.

The rhodium catalyst generally adopted in commercial practice comprises rhodium in complex combination with carbon monoxide and with an organo-phosphorous ligand, for example triphenylphosphine. Although the nature of the catalytic species is not entirely clear, it has been postulated that where the ligand is triphenylphosphine it is HRh(CO)(PPh$_3$)$_3$ (see, for example, page 792 of "Advanced Inorganic Chemistry" (Third Edition) by F. Albert Cotton and Geoffrey Wilkinson, published by Interscience Publishers).

The reaction solution for the hydroformylation reaction will generally contain excess ligand.

U.S. Pat. No. 3,527,809, which is incorporated herein by reference, proposes the use of other ligands, including phosphites, such as triphenylphosphite.

Whilst the use of rhodium catalysts offers various advantages, it does suffer from the disadvantage that it is very expensive. It is therefore desirable to utilise this highly expensive metal in the most economically effective way.

During operation of the reactor, the catalyst may become deactivated and therefore needs to be removed from the reactor such that fresh active catalyst can be added. The removed catalyst will generally be processed to recover the metal values.

The deactivated catalyst may have been thermally deactivated, i.e. clustered and/or chemically deactivated, i.e. poisoned or inhibited.

In some cases although the catalyst may be chemically active, the catalyst solution includes such a high concentration of non-volatile material that it is of no further practical use.

Although the mechanism of deactivation in aryl phosphine liganded systems by the formation of clusters is not entirely clear, it is believed that rhodium clusters, having phosphido bridges may be formed, for example, by the loss of one or more phenyl groups from the aryl phosphine molecule. The formation of clusters is generally increased as the temperature is increased.

The chemical deactivation may be poisoning such as by sulphur compounds, chloride, cyanide and the like.

The chemical deactivation may also be inhibition of the catalyst. Inhibitors that may be found in, for example, propylene and butylene hydroformylation include acetylenes and acroleins.

Since the rhodium catalyst is generally used in low concentration because of its high cost and activity, the effect of any poisons or inhibitors present is high. It is therefore usually necessary to reduce the presence of these poisons and inhibitors present in the feed to very low levels.

Rhodium catalysed hydroformylation processes can be classified into two main categories, namely those in which the aldehyde product is removed by liquid/liquid separation processes and those in which the product is removed by a vapour path process.

In the processes in which the aldehyde product is removed by a liquid/liquid separation process, the aldehyde product is obtained as one liquid phase while the ligand and rhodium/ligand complex remains in another phase and is returned to the reaction zone. This type of process has the advantage of being independent of the volatility of the aldehyde product and the volatility of the relatively less volatile aldehyde condensation by-products. These processes do, however, have their own disadvantages including interphase solubility/entrainment problems in which some of the rhodium may leave in the aldehyde product-containing phase, low selectivity to the desired aldehyde isomer and low reaction rate as a consequence of the low solubility of the reactants in an aqueous base reaction medium.

Where the aldehyde product is recovered from the catalyst by a vapour path process this has conventionally been effected in one of two ways.

Where lower olefin feedstocks are used, a stream of synthesis gas and olefin is passed through the reactor solution, condensed and after separation of the liquid condensate the gas phase is returned to the reactor via a compressor. Suitable means is used to prevent the rhodium solution leaving the reactor by liquid droplet entrainment in the gas phase these include restricting the superficial velocity of the gas through the reactor to less than a specific value and passing the gas/vapour stream through a liquid droplet de-entrainment device before exiting the reactor. Addition of make-up streams of synthesis gas and olefin are required to maintain the system pressure and reaction rate as the reactants are consumed. A purge stream of gas after the condensation stage is generally required to remove any inert gases accumulating in the system and also to control the level of paraffins that either enter the system with the olefin feed or are produced by olefin hydrogenation in the reactor. This type of process is generally known as a Gas Recycle Process.

An important feature of the Gas Recycle Process is that to achieve stable reactor conditions, every product of the reaction must leave the reaction system at it's rate of formation, thus the relatively less volatile materials (such as aldehyde condensation products) accumulate in the reactor solution to a relatively high concentration until the rate of removal of products in the vapour phase equals the production rate of each material. This can be achieved for long periods when the feed olefin is ethylene or propylene but even with propylene there can be a slow accumulation of aldehyde condensation tetramers and pentamers such that the reactor solution volume will slowly increase with time.

If progressively higher olefins such as butenes, pentenes, hexenes etc. are supplied to a gas recycle system the requirement for a higher gas recycle rate means that the gas superficial velocity limit is exceeded unless a reactor solution volume that is increasingly wide and shallow is used as the olefin molecular weight increases. Thus, whilst this arrangement goes some way towards addressing the problems detailed above, the arrangement suffers from new problems associated with gas/liquid mass transfer and reactor mechanical/economic design issues.

In an alternative solution to the problem associated with the use of higher olefins, the temperature of the reaction system is increased such that every component becomes more volatile. Again, whilst this arrangement goes some way to solving the above problem, fresh problems are noted. In this case, increased production of heavy aldehyde self condensation by-products and increased catalyst deactivation by increased clustering rates occurs.

These considerations mean that the Gas Recycle Process is limited to the hydroformylation of ethylene and propylene with the hydroformylation of butenes and pentenes being marginal and very marginal cases respectively.

These considerations led to the development of the so called "Liquid Recycle Process". In this process a volume of solution is continuously withdrawn from the hydroformylation reaction zone or zones such that the liquid level in the or each zone is held constant. This withdrawn liquid is then subjected to a single or multistage evaporation operation where the temperature, pressure and residence times are selected to recover the products and by-products as well as to protect the catalyst activity. The concentrated catalyst solution is then returned to the hydroformylation reaction zone. Olefin and synthesis gas are supplied to the or each hydroformylation reaction zone to maintain the desired reaction rate and conditions.

The liquid recycle process has been shown to provide benefits even for the hydroformylation of propylene where higher volumetric productivity and lower operating costs can be achieved, and is essential for the economic production of $C_5$ and higher aldehydes.

As olefins of increasing molecular weight are hydroformylated by the Liquid Recycle Process the removal of the heavy by-products by evaporation requires lower and lower pressures and/or higher evaporation temperatures. Thus, despite the advantages noted for this process, eventually the accumulation of heavy by-products in the reactor solution occurs such that the reactor volume increases uncontrollably. This disadvantage of the system is referred to as "heavies drowning". Where heavies drowning occurs, there has to be a purge of catalyst solution (containing ligand and active catalyst) to control this accumulation.

It has been suggested, for example in U.S. Pat. No. 5,053,551, that the addition of inert diluents can delay heavies accumulation to defer the heavies drowning effect and confer a longer useful catalyst life. Whilst the system goes some way to addressing the problem, it cannot prevent eventual heavies drowning from occurring.

Thus during the operation of a liquid recycle hydroformylation plant the reaction and product recovery conditions are in a state of continuous change due to the changes in solution composition and catalytic activity. The accumulation of essentially non volatile aldehyde condensation products requires that the pressure and/or temperature of the product evaporator needs progressive adjustment. The accumulation of inhibitors and poisons in the reactor solution also requires the progressive adjustment of reaction conditions to maintain the conversion and selectivity of the system. High temperature evaporation and poisons in the olefin feed can also result in the loss of catalytically active rhodium by poisoning and/or the formation of rhodium clusters requiring the continuous or periodic removal of a part of the catalyst recycle stream and its replacement by fresh catalyst and ligand.

Thus, it will be understood that whichever hydroformylation method is selected, the economic need to run the plant for maximum production of product must be balanced with the need to conserve the life of the expensive catalyst. It is therefore desirable to adopt catalyst management systems which maximise productivity whilst minimising the damage to the catalyst.

One catalyst management system which may be adopted comprises charging a first charge of catalyst to the plant. As the productivity of the plant begins to decline it is necessary to adapt the utilities and separation units of the plant to the reduced flow of aldehyde and the reduced consumption of synthesis gas. Care is taken to ensure that the temperature does not increase since any such increase will result in an accelerated decline in the catalyst activity and increased formation of the heavies. When product flow falls to a level that is unacceptable, the plant operator may choose to raise the temperature with the attendant problems or add additional catalyst.

Although increasing temperature does have the drawbacks detailed above it does not incur the capital expenditure of catalyst purchase and may therefore be the preferred initial approach. Any step change in the temperature will require a corresponding step change in the operation of the utilities and separation units.

After any increase in temperature the productivity will continue to decline but at an increased rate. Further increases in temperature may be carried out until a decision is made that any further increase will result in an unacceptable rate of catalyst deactivation. At this point further catalyst may be added to the reactor. However, increasing the catalyst concentration will also increase the rate of thermal deactivation and the consequential loss of activity. Thus there is an upper practical limit on the amount of rhodium which may be added to the reactor. Eventually it will be necessary to shut down the plant.

One alternative catalyst management system involves taking a continuous purge of the reactor solution which can then be reprocessed to recover the catalyst and remove the heavies. In practice, economics require that the catalyst be reprocessed in large batches and results in significant loss of rhodium metal. This results in high capital expenditure for the plant owners.

Where triphenylphosphine is used as ligand, it may react with the olefin to produce the corresponding alkyldiphenylphosphine. Since the alkyldiphenylphosphines are stronger complexing agents than the triphenylphosphine, a catalyst solution of lower activity and selectivity to the linear product is obtained.

These mechanisms of catalyst degradation become progressively more onerous as the molecular weight of the olefin increases, requiring progressively higher catalyst purge rates.

Conventionally, the operators of the gas or liquid recycle plant have had to collect the active and/or inactive catalyst by shutting down the reactor, removing some or all of the catalyst solution and concentrating it to partially separate it from the other components present. Additionally, or alternatively, partially deactivated or heavies drowned catalyst may be continuously collected from reactor streams. By reactor stream we mean any stream which is obtained from any point in a process and which will contain rhodium metal catalyst. In the case of the liquid recycle process, the stream will usually be the catalyst recycle stream after evaporation of the hydroformylation products.

The conventional liquid recycle process must therefore be subjected to a continuous or episodic regime of adjustment in process conditions throughout the operating period and this is particularly marked when the higher molecular weight olefins are used as feedstock.

Since the rhodium is generally only present at low concentration, it can be particularly difficult and costly to recover the rhodium from the very dilute solutions.

The rhodium organic solution has conventionally been concentrated by a variety of means before being shipped off-site for recovery. This means that if the operation of the plant is not to be shut down for a prolonged period, the operator must purchase more of the very expensive catalyst to operate the plant than he actually requires at any one time.

There are also environmental issues associated with the recovery of the catalyst where phosphorous ligands are present.

A variety of means of recovering the rhodium from solution has been suggested including precipitation followed by extraction or filtration and extraction from the organic mixtures using, for example, amine solutions, acetic acid, or organophosphines.

Ion-exchange methods have also been suggested, for example in U.S. Pat. No. 3,755,393 which describes passing a hydroformylation mixture through a basic ion-exchange resin to recover rhodium. A similar process is described in U.S. Pat. No. 4,388,279 in which Group VIII metals are recovered from organic solution using either a solid absorbent such as calcium sulfate, an anionic ion-exchange resin or molecular sieves.

An alternative arrangement is described in U.S. Pat. No. 5,208,194 in which a process is described for removing Group VIII metals from organic solutions which comprises contacting the organic solution with an acidic ion-exchange resin containing sulfonic acid groups. The treated solution is then separated from the ion-exchange resin and the metal values are recovered from the resin by any suitable means. One means that is suggested is that the resin should be burnt off in an ashing process which leaves the metal in a form suitable for recovery.

These prior art processes, whilst being suitable for separating the metal from the stream in which it was removed from the reaction, suffer from the disadvantage that the operator of the reactor must send the recovered metal concentrate off-site to be converted into an active form. Further, where the stream removed from the reactor includes active catalyst, the separation procedure will either leave it in a form in which it cannot be returned to the reactor or will cause it to be deactivated such that it is no longer suitable for use in the reactor and removal off-site for regeneration is required.

In U.S. Pat. No. 5,773,665, a process is suggested which enables active catalyst contained in a stream removed from a hydroformylation process to be separated from the inactive catalyst and the active catalyst following treatment, to be returned to the hydroformylation reactor. In the process a portion of the recycle stream from the hydroformylation reaction is passed through an ion exchange resin column to remove impurities and active rhodium and the thus purified recycled stream, which may contain inactive catalyst, is returned to the hydroformylation reactor.

The impurities, which may include aryl phosphine oxide, alkyl phosphine oxide, mixed phosphine oxide and high molecular weight organic compounds, are removed from the resin by washing with, for example, an organic solvent. The effluent from this wash is removed as a waste stream. The active catalyst remains bound to the resin during this washing process.

The resin is then treated with a catalyst removal solvent such as isopropanol/HCl to produce a stream containing "active" rhodium catalyst for eventual recycling to the hydroformylation reactor. Whilst the catalyst has not been deactivated by thermal or chemical means and is therefore referred to as "active" it is not in a form in which it will actually act as a catalyst in the reactor. Thus, before the catalyst can be recycled it must first be removed from the resin using a strong acid reagent and then converted to the hydridocarbonyl by treatment with hydrogen and carbon monoxide in the presence of an acid scavenger and a ligand to make it a truly active catalyst.

In an optional arrangement, the inactive rhodium catalyst, i.e. the clustered catalyst, which passed through the ion-exchange resin without being absorbed and which is contained in the purified recycle stream may be reactivated by conventional technology such as by wiped film evaporation followed by oxidation and subsequent reduction before being returned to the reactor. Thus this inactive catalyst is not treated by the ion-exchange resin.

Whilst this process goes some way to improving the conventional hydroformylation process by recycling some of the rhodium, in that it suggests a means of separating the active catalyst on site, it suffers from various disadvantages and drawbacks in particular those disadvantages associated with the need to treat the "active" catalyst after it has been removed from the ion-exchange resin and before it can be returned to the reactor. Indeed it is the ion-exchange treatment which means that the catalyst is no longer suitable for use in the reactor. Although in a preferred embodiment, U.S. Pat. No. 5,773,665 does suggest that the thermally deactivated catalyst may be regenerated before return to the reactor, the overall plant described therein is expensive to construct and operate because of the number of separation and treatment steps required to achieve full recycle. The problem is particularly exacerbated as some of the steps are carried out in the presence of corrosive acid media A further drawback associated with the presence of acid media is the costs associated with the consumption of base required to neutralise the acid.

There is therefore a desire to produce a process for the production, on a continuous basis, of aldehydes from olefins by hydroformylation using a liquid recycle process under constant conditions chosen by the plant operator for extended, preferably indefinite, periods of time whilst providing maximum utilisation of the catalytic metal and ligand.

SUMMARY OF THE INVENTION

Thus according to the present invention there is provided a continuous hydroformylation process for the production of an aldehyde by hydroformylation of an olefin which comprises:

(a) providing a hydroformylation zone containing a charge of a liquid reaction medium having dissolved therein a rhodium hydroformylation catalyst comprising rhodium in combination with carbon monoxide and a ligand;

(b) supplying the olefin to the hydroformylation zone;

(c) maintaining temperature and pressure conditions in the hydroformylation zone conducive to hydroformylation of the olefin;

(d) recovering from the liquid hydroformylation medium a hydroformylation product comprising aldehyde;

(e) recovering from the hydroformylation zone a stream comprising the rhodium catalyst;

(f) contacting at least a portion of the stream with a solid acidic absorbent under process conditions which allow at least some of the rhodium to become bound to the absorbent;

(g) subjecting the rhodium bound to the absorbent, under process conditions which allow desorption of the metal, to a fluid stripping medium comprising hydrogen and solvent;

(h) recovering the rhodium hydride catalyst; and (i) recycling the rhodium hydride catalyst to the hydroformylation zone In a most preferred arrangement, the stream from step (e) is divided and a first part is recycled to the hydroformylation zone and the second part is subjected to steps (f) to (i). Any suitable amount of divided stream may be passed to steps (f) to (i). However, the substantial benefits of the present invention are achievable even if small amounts, such as amounts of the order of 1% or even less such as amounts of the order of 0.01%, are subjected to steps (f) to (i).

It will be understood that the recycled rhodium hydride catalyst from step (i) will be utilised in the further hydroformylation reaction.

The stream recovered from the hydroformylation zone in step (e) may be any stream which is obtained from any point in the hydroformylation process and which will contain rhodium metal catalyst. In the case of the liquid recycle process, the stream will usually be the catalyst recycle stream after evaporation of the hydroformylation products.

The arrangement of the present invention enables substantial benefits to be obtained. First, the recovery and recycling of the present invention enables the plant operator to run the plant with less catalyst than has been required heretofore. This is because it is not necessary to hold catalyst in stock to replace catalyst which is shipped off-site for recovery and regeneration.

The catalyst recovery arrangement of steps (f) to (i) are particularly efficient in separating catalyst from heavies and therefore the system allows for the heavies formation in the reactor or elsewhere in the system to be readily managed without having a deleterious effect on the operation of the reactor. This is because the process of the present invention is particularly suitable for removing the rhodium hydride catalyst from reactor streams containing molecules having a high molecular weight and hence low volatility and which are therefore difficult to separate from the catalyst by conventional means.

Examples of these heavies, which are generally high boiling by-products, include organic condensation products and will include cyclic trimers and higher cyclic moieties and linear and branched polymeric moieties which could also be present in the feed to the reactor.

Further, the presence in the system of the catalyst recycle allows for control of the level of non-volatile inhibitors present in the reactor system and may facilitate long term operation at constant reaction and vaporiser temperatures.

Since the catalyst can be readily recovered and/or heavies readily removed, by the process of the present invention, the plant operator may choose to operate the plant at conditions which have heretofore not been practicable because of catalyst deactivation and/or heavies formation. Thus, for example, higher temperatures in both reactor and vaporiser may be usable which will enable an increased rate of production of the aldehyde.

Thus the present invention provides a hydroformylation process in which continuous recycling of the rhodium catalyst allows for the overall productivity to be maintained constant despite on-going deactivation of the catalyst and heavies formation. As this allows for the previously required step changes in productivity to be obviated, the ease of operation and the efficiency of the reaction is enhanced. The process may also allow feedstocks to be processed which could not be utilised for hydroformylation because of the presence of moieties which would poison and/or inhibit the catalyst or which had a high heavies forming capability.

It will be understood, that these benefits can be obtained either by operating the rhodium recovery steps (f) to (i) continuously or periodically.

The olefin used in the hydroformylation reaction of the present invention contains at least one olefinic carbon-carbon double bond. Preferably the olefin contains from 2 to about 20 carbon atoms although it will be understood that higher olefins may be used. Included within the term "olefin" are not only alpha-olefins, i.e. olefins containing the group —CH=$CH_2$ or >C=$CH_2$ but also internal olefins containing the group —CH=CH—, —$CR_1$=CH—, or —$CR_1$=$CR_1$— where R is an organic moiety, as well as compounds containing both alpha-olefinic and terminal olefinic groups.

Illustrative olefins include olefinically unsaturated hydrocarbons, e.g., alkenes, arylalkenes, and cycloalkenes, as well as substituted olefins, e.g. ethers of unsaturated alcohols, and esters of unsaturated alcohols and/or acids.

Examples of suitable olefins include alpha-olefins (e.g. ethylene, propylene, butene-1, iso-butylene, pentene-1, 2-methylbutene-1, hexene-1, heptene-1, octene-1, 2,4,4-trimethylpentene-1, 2-ethylhexene-1, nonene-1, 2-propylhexene-1, decene-1, undecene-1, dodecene-1, octadecene-1, eicosene-1, 3-methylbutene-1, 3-methylpentene-1, 3-ethyl-4-methylpentene-1, 3-ethylhexene-1, 4,4-dimethylnonene-1, 6-propyldecene-1, 1,5-hexadiene, vinyl cyclohexane, allyl cyclohexane, styrene, alpha-methylstyrene, allylbenzene, divinylbenzene, 1,1-diphenylethylene, o-vinyl-p-xylene, p-vinylcumene, m-hexylstyrene, 1-allyl-4-vinylbenzene, beta-vinylnaphthalene, and the like), alpha-alkenols, (e.g. allyl alcohol, hex-1-en-4-ol, oct-1-en-4-ol, and the like), alpha-alkenyl ethers (e.g. vinyl methyl ether, vinyl ethyl ether, allyl ethyl ether, allyl t-butyl ether, allyl phenyl ether, and the like), alpha-alkenyl alkanoates (e.g. vinyl acetate, allyl acetate, and the like), alkyl alpha-alkenoates (e.g. methyl acrylate, ethyl acrylate, n-propyl oct-7-enoate, methyl methacrylate, and the like), alpha-olefinically unsaturated aldehydes and acetals (e.g. acrolein, acrolein dimethyl and diethyl acetals, and the like), alpha-olefinically unsaturated nitriles (e.g. acrylonitrile, and the like), and alpha-olefinically unsaturated ketones (e.g. vinyl ethyl ketone, and the like). The term olefin also includes internal olefins which contain preferably from 4 to about 20 carbon atoms. Such compounds have the general formula:

$$R_1R_2C=CR_3R_4$$

in which $R_1$ and $R_2$ each represent a hydrogen atom or an organic radical or together represent a divalent radical which, together with the indicated carbon atoms, form a carbocyclic or heterocyclic ring, and $R_3$ and $R_4$ each represent an organic radical or together represent a divalent radical which, together with the indicated carbon atoms, form a carbocyclic or heterocyclic ring.

As examples of internal olefins there may be mentioned cis- and trans-butene-2, 2-methylbutene-2, 2,3-dimethylbutene-2, 1,2-diphenylethylene, hexene-2, hexene-3, cis- and trans-heptane-2, decene-2, tetradecene-2, 4-amyldecene-2, 4-methyltridecene-2, octadecene-2, 6,6-dipropyldecene-3, prop-1-enylbenzene, 3-benzylheptene-3, cyclobutene, cyclopentene, cyclohexene, cycloheptene, cyclooctene, 1-methylcyclohexene, diethyl maleate, diethyl fumarate, crotonaldehyde, crotonaldehyde dimethyl acetal, ethyl cinnamate, cis- and trans-prop-1-enyl t-butyl ether, and the like.

The hydroformylation reaction may be carried out on a mixture of 2 or more olefins.

The or each olefin selected for the hydroformylation reaction will be charged to the hydroformylation zone where it will be contacted with hydrogen and carbon monoxide. One or more inert materials, such as inert gases (e.g. nitrogen, argon, carbon dioxide and gaseous hydrocarbons, such as methane, ethane, and propane) may also be present. Such inert gases may be present in the olefin feedstock, the synthesis gas or both. Other inert materials may include hydrogenation by-products of the hydroformylation reaction, for example n-butane where the olefin is butene-1 or butene-2 and corresponding alkanes for other olefin starting materials.

The process may be operated so that apart only of the olefin, e.g. from about 15% to about 80% or higher, is converted in passage through the hydroformylation zone. Although the process can be operated on a "once through" basis, with unreacted olefin being exported, possibly for other uses, after product recovery, it may be desirable to recycle unreacted olefin to the hydroformylation zone.

As some isomerisation of olefin may occur in passage through the hydroformylation zone (for example in the case of butene-1 some isomerisation to butene-2 may occur) when using $C_4$ olefins or higher, the recycle olefin stream may in such cases contain a minor amount, typically about 10% or less, of isomerised olefin, even though the olefin feedstock is substantially free from other isomeric olefin(s). In addition it may contain by-product hydrogenated feedstock. The concentration of isomerised olefin(s) and of inert materials in the recycle stream or streams can be controlled in the conventional manner by talking purge streams at appropriate controlled rates.

The feed of the olefin may be a mixed feedstock containing both internal and alpha-olefin components. For example, it is possible to use a mixed $C_4$ hydrocarbon feedstock containing, in addition to cis- and trans-butene-2, also butene-1, iso-butylene, n-butane, iso-butane, and minor amounts of $C_{1-5}$ alkanes.

The olefin may be subjected to any suitable pretreatment before being charged to the hydroformylation zone. However, the ability of the process of the present invention to readily remove heavies and regenerate catalyst means that pretreatment to remove impurities and the like from the hydroformylation zone may not be required or may be reduced.

Thus, for example, in prior art arrangements, the presence of a rhodium poison or inhibitor at a level of about 0.5 gram equivalent of rhodium per cubic meter of feed, will result in complete deactivation in a period of the order of 200 days. With the present invention, this presence in the feed of this level of poisons and/or inhibitors may be readily accommodated.

The rhodium hydride catalyst used in the process of the present invention is preferably a rhodium carbonyl complex comprising rhodium in complex combination with triphenylphosphine, triphenylphosphite or other phosphorous ligands for example those described in U.S. Pat. No. 4,482,749 which is incorporated herein by reference. Triphenylphosphine is particularly preferred.

The rhodium may be introduced into the reaction zone in any convenient manner. For example, the rhodium salt of an organic acid, such as rhodium acetate, i.e. $[Rh(OCOCH_3)_2.H_2O]_2$, can be combined with the ligand in the liquid phase and then treated with a mixture of carbon monoxide and hydrogen, prior to introduction of the olefin.

In one alternative arrangement the catalyst can be prepared from a carbon monoxide complex of rhodium, such as dirhodium octacarbonyl, by heating with the ligand which thereby replaces one or more of the carbon monoxide molecules. It is also possible to start with the ligand of choice and finely divided rhodium metal, or with an oxide of rhodium (e.g. $Rh_2O_3$ or $Rh_2O_3.H_2O$) and the ligand, or with a rhodium salt of an inorganic acid, such as rhodium nitrate (i.e. $Rh(NO_3)_3.2H_2O$) and the ligand, and to prepare the active species in situ during the course of the hydroformylation reaction.

In another alternative embodiment, it is possible to introduce into the reaction zone, as a catalyst precursor, a rhodium complex such as (pentane-2,4-dionato) dicarbonyl rhodium (I) which is then converted, under the hydroformylation conditions and in the presence of excess ligand, to the operative species. Other suitable catalyst precursors include $Rh_4(CO)_{12}$ and $Rh_6(CO)_{16}$.

The rhodium complex catalyst is preferably dissolved in the liquid reaction medium which comprises, in addition to the catalytic species, olefin, and a predetermined level of the phosphorous ligand.

Once the plant is operational the reaction medium may also comprise some or all of product aldehyde(s), aldehyde condensation products, isomerised olefin and hydrogenation product(s)derived from the olefin. The inert material detailed above may also be present. The nature of the aldehyde condensation products, and possible mechanisms for their formation during the course of the hydroformylation reaction, is explained in more detail in GB-A-1338237, which is incorporated herein by reference.

Additionally the reaction medium may comprise a solvent, such as benzene, toluene, acetone, methyl iso-butyl ketone, t-butanol, n-butanol, tetralin, decalin, ethyl benzoate and the like.

Usually, however, it will be preferred to operate in a "natural process solvent", i.e. a mixture of olefin or olefins, hydrogenation product(s) thereof, aldehyde product(s) and aldehyde condensation products. In addition, solvent from catalyst recovery may be present. However, when operating continuously or semi-continuously, it may be preferred to use at start up a solvent, such as acetone, benzene, toluene, or the like, and then gradually to allow this to be displaced by "natural process solvent" by differential evaporation as the reaction progresses.

The rhodium concentration in the liquid reaction medium may vary from about 10 ppm or less up to about 1000 ppm or more, calculated in each case as rhodium metal and on a weight/volume basis. Typically the rhodium concentration in the liquid reaction medium lies in the range of from about 40 ppm up to about 200 ppm, calculated as rhodium metal. For economic reasons it will not usually be desirable to exceed about 500 ppm rhodium, calculated as metal, in the liquid reaction medium.

In the liquid reaction medium the ligand:Rh molar ratio is 1:1 or greater but will be limited by solubility constraints.

Make-up ligand may be added and the addition may be continuous or intermittent. It may be added as the essentially pure compound or as a solution in a suitable solvent, e.g. one of the solvents previously mentioned. If continuous addition is chosen then it can be added in solution form with the aid of a suitable dosing pump.

The hydroformylation conditions utilised in the process of the present invention involve use of elevated temperatures e.g. in the range of from about 40° C. to about 160° C. or more. Conventionally it will be preferred to operate at as low a temperature as is possible i.e. from about 70° C. to about 95° C. as this will enable a satisfactory reaction rate to be achieved while minimising the risk of heavies formation.

Although the use of higher temperatures has heretofore been disadvantageous because of catalyst deactivation and/or heavies formation, the process of the present invention, which allows for ready recycle and reactivation of the catalyst, means that deactivation and/or heavies formation is not disadvantageous and the higher temperatures will generally enable improved reaction rates. Thus temperatures in the range of from about 95° C. to about 150° C. or higher may be used.

Thus, for example, in prior art arrangements, an uneconomic system is reached where the hydroformylation of the olefin results in a heavies concentration with a recycle stream of greater than 60 wt % within a period of 200 days, through either the use of elevated temperatures and/or presence of involatile material in the feed or formed in the reaction system. In contrast, in the present invention, this level of heavies may be accommodated.

Elevated pressures are also typically used in the hydroformylation zone. Typically the hydroformylation reaction is conducted at a total pressure of from about 4 bar upwards up to about 75 bar or more. Usually it will be preferred to operate at a total pressure of not more than about 35 bar.

In operating the process of the invention in a continuous manner it is desirable to supply make up amounts of hydrogen and carbon monoxide in an approximately 1:1 molar ratio, for example about a 1.05:1 molar ratio. The formation of such mixtures of hydrogen and carbon monoxide can be effected by any of the methods known in the art for producing synthesis gas for hydroformylation, e.g. by partial oxidation of a suitable hydrocarbon feedstock such as natural gas, naptha, fuel oil or coal.

In operating the process of the invention the total pressure of hydrogen and carbon monoxide in the hydroformylation zone can range from about 1.5 bar or less up to about 75 bar or more. The partial pressure of hydrogen may exceed that of carbon monoxide, or vice versa. For example the ratio of the partial pressures of hydrogen and of carbon monoxide may range from about 10:1 to about 1:10. In general, it will usually be desirable to operate at a partial pressure of hydrogen of at least about 0.05 bar up to about 30 bar and at a partial pressure of carbon monoxide of at least about 0.05 bar up to about 30 bar.

Product recovery can be effected in any convenient manner. In some instances, for example when using butene-1 or butene-2 as the olefinically unsaturated compound, it is possible to utilise a gas recycle process similar to that described in GB-A-1582010 which is incorporated herein by reference.

More usually, however, it will be convenient to withdraw a portion of the liquid reaction medium from the hydroformylation zone either continuously or intermittently and to distil this in one or more stages under normal, reduced or elevated pressure, as appropriate, in a separate distillation zone in order to recover the aldehyde product(s) and other volatile materials in vaporous form;

the rhodium-containing liquid residue being recycled to the hydroformylation zone either directly or via process steps (f) to (i).

Condensation of the volatile materials and separation thereof, e.g. by distillation, can be carried out by any conventional means. Aldehyde product(s) can be passed on for further purification, whilst a stream containing unreacted olefin can be recycled to the hydroformylation zone together with any hydrogen and carbon monoxide dissolved in the reaction medium. A bleed stream can be taken from the recycle stream or streams in order to control build up of inerts (e.g. $N_2$) and of hydrogenation product(s) in the recycle streams.

When using aldehyde condensation products as solvent, the ratio of aldehyde to such products in the liquid reaction mixture in the hydroformylation zone may vary within wide limits. Typically this ratio lies in the range of from about 1:5 to about 5:1 by weight.

Under appropriate conditions aldehyde productivities in excess of about 0.5 g. mole/liter/hr can be achieved in the process of the invention. Hence it is usually preferred to supply make up olefin to the hydroformylation zone at a rate which corresponds to the aldehyde productivity of the system under the hydroformylation conditions selected. As the conversion per pass will usually be less than 100%, typically about 15% to about 80% or higher, it will be necessary to increase correspondingly the feed rate of the make up olefin if the process is to operate on a "once through" basis or to recycle unreacted olefin at an appropriate rate if the process operates with olefin recycle. Often the aldehyde productivity rate exceeds about 1.0 g. mole/liter/hr, e.g. up to at least about 2 g. moles/liter/hr and the rate of supply of make up olefin must then equal or exceed this value.

At least one stream removed from the reactor will be subjected to the catalyst recovery steps (e) to (i).

The reactor stream may be any stream which is obtained from any point in the hydroformylation reaction process and which will contain metal hydride catalyst in solution. Thus catalyst may be removed from the reactor, in product stream or in other streams including purge streams. These streams may be treated in accordance with steps (e) to (i) of the present invention to recover the catalyst in a form which is suitable for return to the reactor. The whole of the stream may be subjected to the steps or the stream may be split and a portion thereof subjected to steps (e) to (i). The remainder of the stream may be recycled to the reactor.

The reactor stream or a part thereof may be passed directly for treatment in accordance with steps (e) to (i) or may first undergo any suitable pretreatment. Where the reactor stream is a product stream, the reaction product may be present during the recovery process of the present invention or may be removed at least partially before the stream is contacted with the absorbent.

The various streams from the reactor, following suitable pre-treatment, such as to remove product may be combined for treatment through a single plant suitable for steps (e) to (i). Alternatively, each stream may be treated separately or streams with similar compositions may be treated together.

The fluid stripping medium of step (g) may comprise hydrogen and a process compatible solvent in a single fluid phase, which may be a supercritical phase. In one alternative arrangement the fluid stripping medium comprises hydrogen and a process compatible solvent in a two phase system. In one arrangement, the process compatible solvent may be a solvent or reactant of the reaction.

Where the fluid stripping medium comprises a liquid phase and a gas phase, the ratio of the gas phase to the liquid phase may be any suitable value. One suitable example would be one volume of gas to ten volumes of liquid.

Where the fluid is a single phase, the ratio of dissolved hydrogen to solvent present may be any suitable value and may be similar to that used for the two phase system. An important parameter is that an appropriate amount of hydrogen is present.

In one arrangement, the solvent is a liquid which is contacted with a gas phase including hydrogen until it is partially or totally saturated with dissolved gases. The liquid may then be separated from the gas phase prior to being passed over the metal containing absorbent as a single phase. The saturated solution may be increased in pressure before being passed over the absorbent as the stripping medium.

Supercritical propane or carbon dioxide may be used as process compatible solvent. In this arrangement, a supercritical mixture including hydrogen, an optional co-solvent, and ligand may be used as the stripping fluid.

In a preferred arrangement of the present invention the acidic absorbent is an acidic ion exchange resin. The resin may be a styrene divinylbenzene copolymer containing sulphonic acid groups or carboxylic acid groups. The resin may have a siloxane-containing backbone and an acidic functional group attached to the backbone. The acidic functional group is preferably selected from the group consisting of aromatic carboxylic acids, aliphatic carboxylic acids, aromatic sulphonic acids and aliphatic sulphonic acids, with the sulphonic acids being particularly preferred.

Preferably the resin is used in the protonated form. Thus where the sulphonic acid groups are the active groups, they are in the form —$SO_3H$ and in the presence of phosphines they are at least partially in the form —$SO_3^{(-)}[HPR_3]^{(+)}$. Neutralized sulphonic acid resins, in which some or all of the protons have been exchanged by a cation may also be suitable but are not preferred.

Particularly preferred resins include Amberlyst™ 15 and Amberlyst™ DPT-1, with Amberlyst™ DPT-1 being most preferred. Amberlyst™ 15 is available from Rohm and Haas (U.K.) Limited of Lennig House, 2 Mason's Avenue, Croydon CR9 3NB, England and Amberlyst™ DPT-1 ion exchange resin is available from Kvaerner Process Technology Limited of The Technology Centre, Princeton Drive, Thornaby, Stockton-on-Tees TS17 6PY, England.

The absorbent may be pre-treated prior to use. The absorbent may be washed, for example, with methanol to remove water and may also be sieved prior to being contacted with the reactor stream.

Without wishing to be bound by any theory, it is believed that the ion-exchange resin or other suitable absorbent will allow the absorption of the metal hydride species onto its surface by a protonation and subsequent elimination of hydrogen by the following reaction:

$$HRh(X)_n + -SO_3H \rightleftharpoons -SO_3Rh(X)_n + H_2$$

where each X is a liganding group which may be the same or different and n is an integer of from 2 to 5.

This hydrogen elimination is a reversible reaction and thus the metal species remains as a labile species and can be desorbed by the hydrogen in the fluid stripping medium.

Whilst the reactor stream may be contacted with the solid absorbent by any suitable means, the absorbent is preferably a resin bed in a column through which the reactor stream flows. Once the resin bed has been loaded with the metal, the stripping medium is then preferably passed through the resin bed and into the reactor. In one alternative arrangement, the reactor stream may be contacted with the absorbent in a stirred vessel. In this arrangement, the contact will be a repeated batch process.

The contact of the reactor stream with the solid acid absorbed resin may be carried out at any suitable temperature. Temperatures of from 0° C. to about 120° C. may be used with those of from about 20° C. to about 100° C. being preferred. A temperature in the region of from about 50° C. to about 95° C. is particularly preferred as the higher temperature will facilitate the removal of the metal from solution and its loading onto the absorbent. The temperatures and pressures will generally be selected such that any solids formation such as crystallisation of ligand or ligand oxide is avoided.

As the catalyst is absorbed onto the resin, a catalyst depleted solution will remain and may be removed from the system. The further treatment of this solution will depend on the content of the stream. Where the reaction stream treated in accordance with the present invention is a stream containing heavies, the catalyst depleted solution will preferably be removed. The catalyst depleted solution may be passed through a conventional catalyst collection system to trap the inactive catalytic metal and any trace amounts of the catalyst remaining.

The stream to be treated may be concentrated before being contacted with the acidic absorbent. The concentration will preferably occur by removal of volatilisable material. The reactor stream or the concentrated stream may require dilution with a solvent compatible with the absorbent before it is contacted with the absorbent. Any suitable solvent may be used. Normally, the solvent will be miscible with the reactor stream or concentrated stream. Suitable solvents include xylene and toluene.

Where the stream to be treated includes inactive catalyst this may be exposed to the absorbent but may not react therewith and if no reaction occurs will be removed with the non-volatile components.

However, where the inactive catalyst has been deactivated by the formation of clusters, these may be broken before the stream is contacted with the absorbent such that they can be absorbed by the absorbent and treated with the stripping medium. By this means this inactive catalyst may be regenerated such that it may be returned to the reactor and take part in the reaction.

Thus according to a preferred aspect of the present invention, the stream is preferably passed through an oxidiser where air is passed through the solution to break down the clusters before being brought into contact with the absorbent. For a rhodium catalyst having triphenylphosphine as a ligand, the air will break down the rhodium clusters by oxidation of the phosphido bridges.

The oxidiser may also at least partially oxidise any trivalent phosphorous compounds which may be present to the pentavalent form (i.e. conversion from phosphites to phosphates).

Where the oxidiser is present, the oxidation step, in addition to breaking up the clusters, may additionally change the oxidation state of the metal in that it will be converted to a simple cationic form. Thus $Rh^{2+}$ and $Rh^{3+}$ will be formed.

Additionally or alternatively, the reaction stream may be treated in accordance with one or more of the organic reagents described in U.S. Pat. No. 4,929,767 and U.S. Pat. No. 5,237,106 which are incorporated herein by reference.

To improve the absorbability of the rhodium onto the absorbent, the process may additionally include, treating the catalyst such that it is in a suitable state for absorption. The catalyst preferably is subjected to hydrocarbonylation where it is treated with an organophosphorous ligand such as triphenylphosphine, carbon monoxide and hydrogen to reform the catalyst in the form $Hrh(CO)(PPh_3)_3$.

Once the rhodium has been loaded onto the absorbent, the absorbent may be washed to further remove impurities. In addition to removing impurities by means of their not being absorbed by the absorbent such that they are removed in the catalyst depleted reactor stream or by the washing described above, the absorbent may also serve to remove some impurities. For example, iron, nickel and/or chromium may be present. These will generally also be absorbed by the absorbent but will not be retrieved by the stripping medium of the present invention. Thus the stream recycled to the reactor will be free of these impurities.

Whatever pre-treatments of the stream are carried out, and whatever washing is carried out, if any, the partial pressure of the gaseous phase of the stripping media, or of the hydrogen component of the supercritical phase or the fluid phase, for removing the absorbed metal may be of any suitable value. Partial pressures of about 200 kPa or higher may be particularly advantageous. The upper limit on the partial pressure will be dictated by the equipment rating.

The stripping media fluid preferably additionally includes carbon monoxide. The presence of carbon monoxide has been found to offer improved results and is particularly appropriate as the catalyst complex includes CO as a ligand.

The fluid of the stripping media preferably includes a liquid phase which comprises liquids which are compatible with the reactants, other compounds and products in the hydroformylation zone, such that the product stream containing the rhodium catalyst may be returned to the reactor without further processing. The fluid is preferably also compatible with product recovery operations.

In one embodiment of the present invention, the fluid of the stripping media will comprise liquids which are required to be present in the hydroformylation zone such as ligands and raw materials. Thus, where the catalyst is $HRh(CO)(PPh_3)_3$ in one arrangement, the liquid phase will comprise triphenylphosphine. Additionally or alternatively, the liquid phase may comprise olefin and/or triphenylphosphine. Thus, a preferred process of the present invention allows that no additional substances are fed to the hydroformylation zone other than those required for or produced in the hydroformylation reaction.

In one alternative embodiment, the fluid includes material that is used in the catalyst recovery process but which is inert to the hydroformylation process. The material is preferably recoverable and recyclable from the hydroformylation zone to the rhodium recovery section of the plant. One example of suitable material is toluene which may be used as a solvent or diluent in the rhodium recovery process.

Whilst the reactor stream may be contacted with the solid absorbent by any suitable means, the absorbent is preferably a resin bed in a column through which the stream collected in step (e) flows. Once the resin bed has been loaded with the rhodium, the stripping medium is then preferably passed through the resin bed and into the reactor.

The stripping process will preferably simultaneously regenerate the absorbent bed for further subsequent absorption of rhodium from a fresh stream. However, it may be advisable to wash the resin at least periodically to remove any impurities, ligand and the like which may build up over several passes of the reactor stream.

The stripping may be carried out at similar temperatures to those used for the loading. However, lower temperatures favour the rhodium being desorbed and going into solution. Suitable temperatures include from about 20° C. to about 70° C. This is particularly the case where higher partial pressures of hydrogen are used.

To allow for continuous treatment of catalyst from the reactor, the plant may include at least two beds of absorbent operated in parallel. The reactor stream will be passed through a first bed of absorbent such that the rhodium is substantially removed from the stream. Once the bed has been loaded, the stream will be switched to flow through the second bed. Whilst the second bed is being similarly loaded, the stripping medium will be applied to the first bed such that the rhodium is desorbed. The procedure will then be reversed such that the first bed is being loaded while the second bed is being desorbed. Thus in a preferred arrangement, the process is effectively continuous.

Thus the present invention provides a process the plant for which is cost-effective to construct and to operate and which enables the catalyst to be recovered from reactor streams and returned to the reactor.

A further advantage of the present invention is that where reactants, ligands and the like are used for the stripping medium and these are passed via the absorbent where stripping occurs, to the reactor, not only are no additional substances, or only inert substances, introduced into the reactor, there are no costs associated with the stripping medium.

The recovery of the catalyst in accordance with the present invention may also enable poisoned and/or inhibited catalyst to be reactivated. Without wishing to be bound by any theory, it is believed that the metal is attracted to the absorbent and the poison/inhibitor is removed in the catalyst depleted stream.

BRIEF DESCRIPTION OF THE DRAWINGS

The present invention will now be described, by way of example with reference to the accompanying drawings in which.

DETAILED DESCRIPTION OF THE DRAWINGS

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
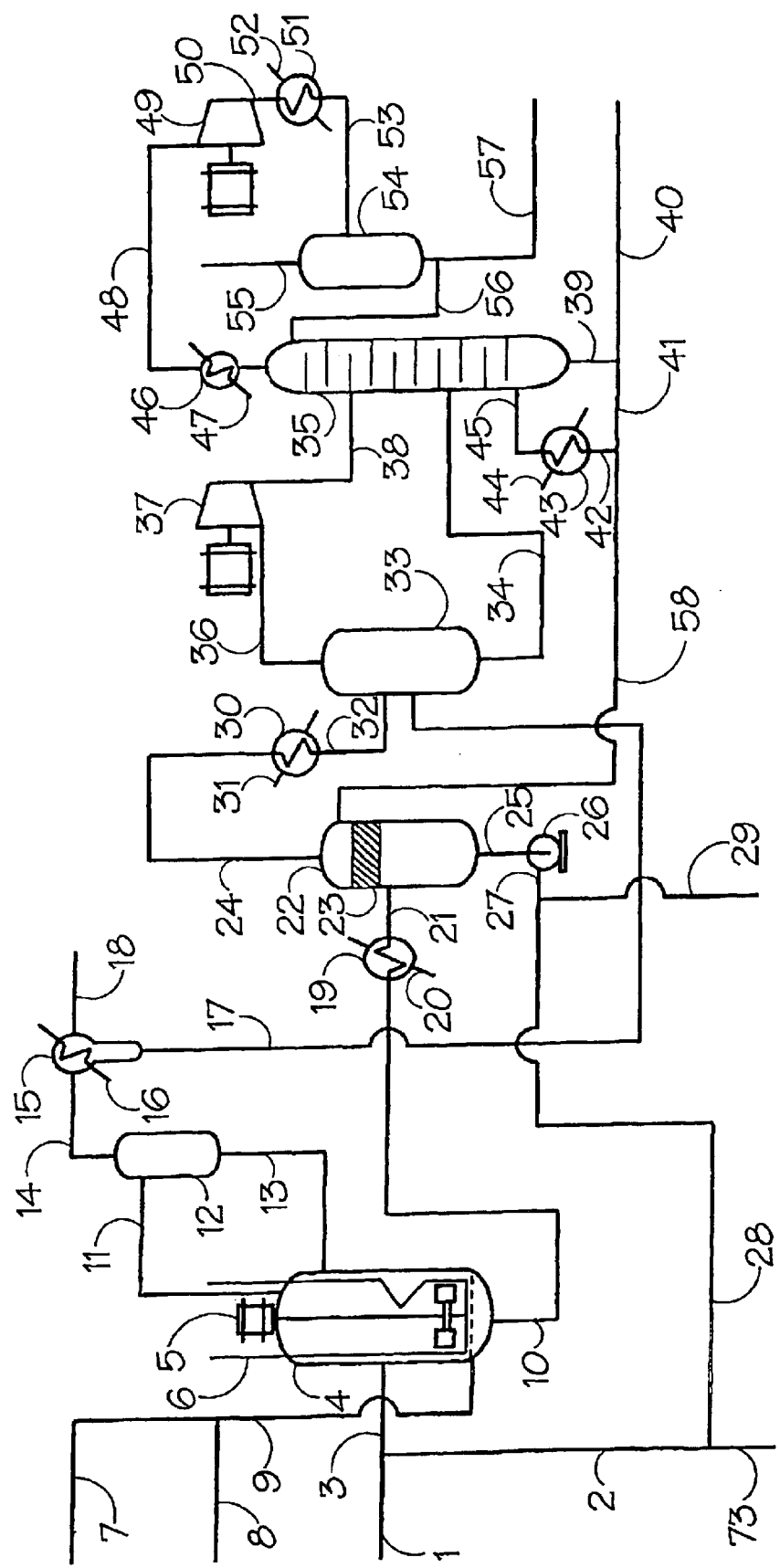
FIG. 1 is a schematic diagram embodying the process in accordance with the present invention.

As illustrated in FIG. 1, a liquid comprising olefin is fed to the apparatus in, line 1 where it is joined by a catalyst solution in line 2. The mixed liquids continue in line 3 to the reactor 4. The reactor is fitted with an agitator 5 which is capable of inducing the gas from the reactor head space into the liquid and anti liquid vortex baffles (not shown). The reactor is also equipped with an internal cooling coil 6 arranged such that a controlled flow of a fluid enables the reactor to be maintained at the desired temperature. Generally an external electrical heater (not shown) is used for the start-up of the equipment.

The reactor 4 is supplied with a 1:1 molar ratio mixture of carbon monoxide and hydrogen in line 7. A trim stream of carbon monoxide and/or hydrogen is supplied in line 8 so that the ratio of the gas partial pressures in the reactor head space can be adjusted to any desired value. The gas stream 9 is sparged into the base of the reactor. The unreacted gases pass out of reactor 4 by line 11. This stream passes to demister vessel 12 where any catalyst containing liquid droplets are collected to return to reactor 4 by line 13.

The gases continue by line 14 to condenser 15 supplied with a coolant fluid in line 16. The resulting condensate passes via line 17 to product recovery and the uncondensed gases pass from the system in line 18.

The liquid leaves the hydroformylation reactor 4 and passes to the product recovery equipment by line 10. Level control devices (not shown) ensure that a constant liquid inventory is maintained in the reactor.

The liquid in line 10 comprising of catalyst components, hydroformylation products, unreacted olefin feed, hydrogenated, isomerised and unreacted olefin, as well as aldehyde condensation products with some dissolved gases passes into vaporiser 19 supplied with a heating fluid in line 20.

The mixture of liquid and vapour passes via line 21 into vapour/liquid separation vessel 22. Vessel 22 is equipped with droplet agglomeration device 23 which is irrigated by a small stream of product from line 58 to wash any ligand and rhodium values back into the base of vessel 22.

The vapour leaves by line 24 and the liquid leaves by line 25. The liquid in line 25 which is now free of vapour and which comprises catalyst is pumped by catalyst recycle pump 26 into line 27. A major portion of the catalyst solution is recycled in line 28 via line 2 to the reactor 4. It will generally be mixed with any fresh feed from line 1 prior to its addition to reactor 4.

A minor portion of the stream in line 27 is passed in line 29 to the rhodium recovery unit. Stream 73 will generally comprise recovered and make up rhodium, recovered and/or make up triphenylphosphine (or other ligand) as well as solvents and hydroformylation reaction by-products.

The vaporisation conditions of temperature and pressure are adjusted such that the liquid level in vessel 22 is constant and this sets the total liquid inventory of the reaction system.

The vapours in line 24 pass to condenser 30 which is supplied with coolant in line 31. The cooled mixture then leaves by line 32 and joins the liquid from line 17 in product vessel 33. The liquid passes from vessel 33 via line 34 to distillation column 35. The vapour from vessel 33 passes through line 36 to compressor 37 and then in line 38 to distillation column 35. The compressor 37 and its associated control equipment (not shown) determines the pressure in vessels 22 and 33 and hence the product vaporisation temperature in vaporiser 19.

In column 35, which is illustrated with distillation trays, the aldehyde products are recovered as bottom products in lines 39 and 40. Some aldehyde product recirculates through lines 41, 42 and 45 via reboiler 43 provided with a heating fluid in line 44. The heating fluid provides the energy supply for the distillation.

The overhead vapours from column 35 are partially condensed in reflux condenser 46 provided with cooling coil 47.

The uncondensed vapours pass on in line 48 through compressor 49, line 50 and condenser 51 with cooling coil 52. This arrangement determines the pressure in the distillation system as well as providing a higher pressure in the condenser 51.

The liquid and gas pass by line 53 to separator 54. The gases leave the system by line 55. The liquid is partially returned as reflux to the upper part of column 35 by line 56 and the nett make of liquid is recovered in line 57. This liquid can comprise any volatile solvents added as part of stream 73 which is added into line 28 as well as comprising unreacted and isomerised olefin and paraffin or other volatile components of the olefin feed stream 1. This stream (after optional further processing) can for example be used in the rhodium recovery and recycle section of the equipment.

In use, the equipment is brought into operation by flushing all oxygen from the system with nitrogen or argon. Then by filling the reactor 4 and vessel 22 with a liquid such as toluene (or pure aldehyde if available) containing dissolved ligand such as triphenylphosphine and a rhodium catalyst precursor complex (such as rhodium dicarbonyl acetylacetonate). A liquid recirculation through the reactor 4, vessel 22 and lines 25, 28, 2 & 3 is established by pump 26.

Olefin feed is supplied at a low rate to the system via line 1 and carbon monoxide plus hydrogen by line 7. The reactors are warmed towards operating temperature and the liquid inventory in the system maintained by vaporising liquid in vaporiser 19 as required.

When the reaction starts, which can be noted on instrumentation as gas uptake, the product aldehyde accumulates in the system and the start-up solvent preferentially leaves. The distillation equipment is commissioned and solvent progressively leaves the system.

Eventually aldehyde starts to accumulate in the base of column 35. Pressures and temperatures are adjusted until normal operating conditions are attained and aldehyde product leaves in line 40. When heavies start to accumulate in the catalyst recycle solution which can be determined by analysis of the composition of line 27, a stream of material is taken from line 29, treated as described below and recovered and with make-up material returned in line 73.

Figure 2:
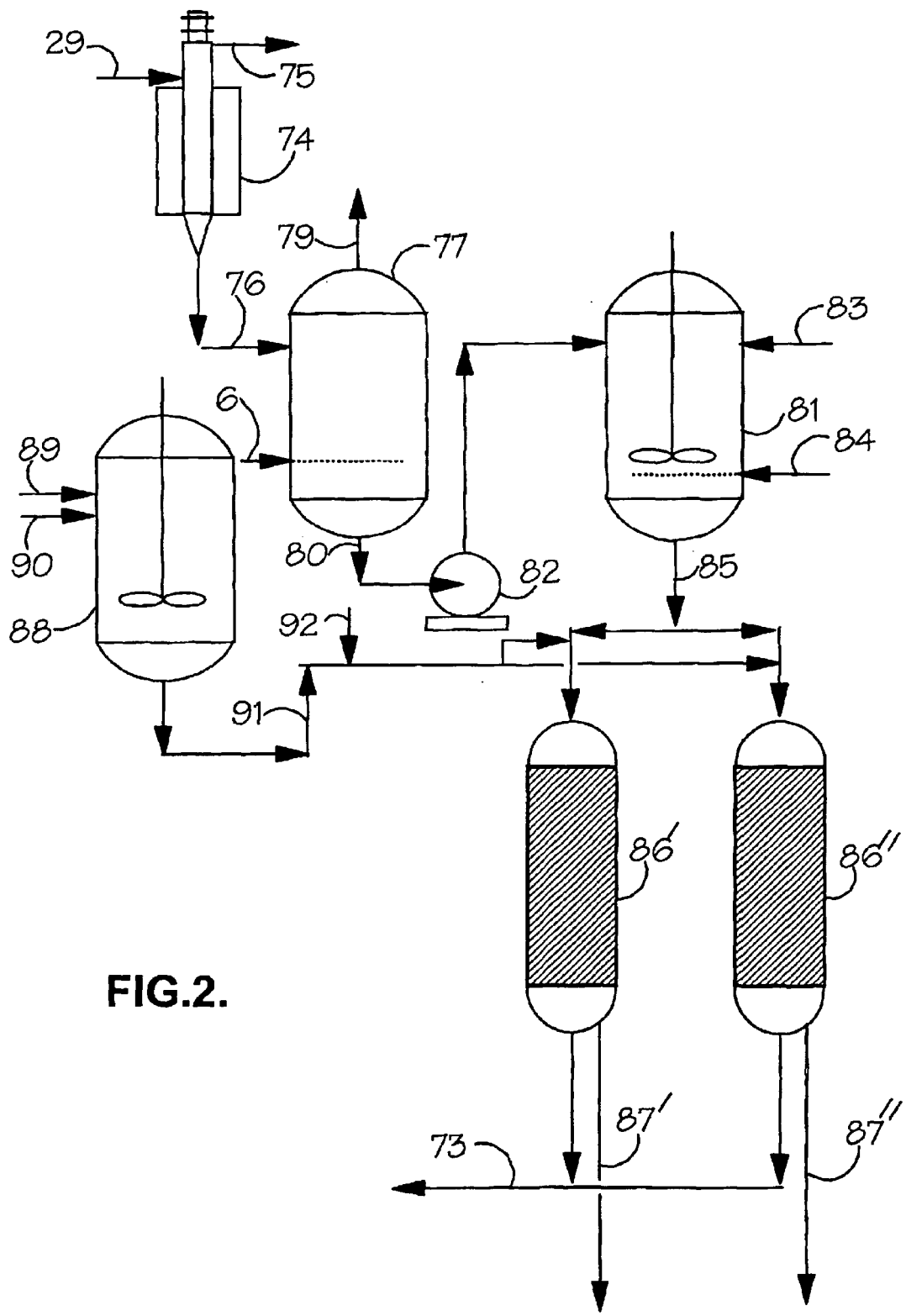
FIG. 2 is a schematic diagram embodying steps (e) to (i) of the present invention.

Stream 29 is then passed to the rhodium recovery zone which is illustrated in FIG. 2. This stream 29 will first be passed to an evaporator 74, such as a wiped film evaporator, to separate any remaining volatile components. Volatile components of the stream will be removed in line 75 and may be subjected to further treatment including condensation and separation. Triphenylphosphine may also be removed in line 75.

The residue of unvaporized portions which will now be a concentrated stream is passed in line 76 to oxidiser 77 where air is bubbled through the liquid. The air is introduced in line 78 and is purged in line 79. The air will serve to break any cluster rhodium molecules so that this previously inactive rhodium can be absorbed by the ion exchange resin.

The stream including the rhodium leaves the oxidiser in line 80 and is then pumped, by pump 82, to a hydrocarbonylation zone 81. In this stirred tank vessel, the catalyst containing stream is mixed with triphenylphosphine added in line 83 and is contacted with hydrogen and carbon monoxide which is added in line 84. The triphenylphosphine added via line 83 may be recycled triphenylphosphine recovered from line 75.

The carbonylated catalyst is then removed in line 85 and is passed into the first absorber column 86' which is packed with ion-exchange resin Amberlyst™ DPT-1. The resin bed will be at a temperature in the region of about 75° C. to aid the rate of absorption of the rhodium by the ion-exchange resin.

As the stream passes through the absorbent bed, the rhodium is absorbed onto the resin and the non-volatile heavies and impurities are removed in stream 87' for optional further processing. Due to the value of the rhodium, the stream may be passed through a conventional rhodium recovery system (not shown) to collect any catalyst which may pass through the resin bed, which may be inactive catalyst, for off-site regeneration.

Once column 86' has been loaded, the stream from vessel 81 will be directed to column 86" so that the removal of the rhodium can be carried out as a continuous process. When the resin is loaded in column 86", the catalyst depleted stream is removed in stream 87".

The rhodium loaded in column 86' is then stripped from the resin using a stripping medium which is passed through the column. Where the stripping medium contains a mixture of organic liquids, these will be combined in mixer 88. The liquid phase is preferably a combination of process compatible solvents and/or olefin added in line 89 and triphenylphosphine added in line 90.

The olefin may be fresh olefin which will be passed through the resin bed before being added to the reactor. Alternatively, the olefin may be recycled olefin, isomerised olefin and paraffin recovered from streams removed from the hydroformylation reaction zone.

Similarly, the process compatible solvents may be fresh solvents or recycled solvents recovered from streams removed from the hydroformylation reaction zone or the downstream product recovery systems.

The triphenylphosphine may be fresh triphenylphosphine or it may be recycled, for example from stream 75 of volatile compounds removed from the wiped film evaporator 74.

This combined liquid phase for the stripping medium is removed from the mixer 88 in line 91 where it is combined with hydrogen and carbon monoxide of the gaseous phase which is added in line 92. The stripping medium will be passed through column 86' which is held at ambient or higher temperature.

The resulting stream, which will contain rhodium, hydrogen, carbon monoxide, triphenylphosphine and olefin and/or process compatible solvents is then returned to the reactor in line 73.

The removal of the rhodium allows resin bed 86' to be used to absorb further rhodium. Resin bed 86" can then be stripped by repeating the process described above. Thus the process can be operated in a continuous manner.

Whilst the present invention has been illustrated with one reactor, vaporiser, etc., it will be understood that where appropriate the numbers of some or all of these could be increased.

The invention is illustrated further in the following Examples.

COMPARATIVE EXAMPLE 1

Hydroformylation is carried out on 1-decene in a hydroformylation plant as described above is run with a rhodium concentration in the reactor of 220 ppm, a triphenylphosphine concentration of 10 wt %, hydrogen and carbon monoxide partial pressures each at 30 psi and at a reactor temperature of 110° C. such that non-volatile components gradually build up in the recycle loop. No material is taken in line 29 for catalyst recycle and the system is run until the shut down criterion of excess heavies in the catalyst recycle solution is reached. The design of the plant apparatus imposes a maximum content of heavies material in the recycle. For the purposes of these examples, the maximum heavies content is taken to be 60 wt %. When this point is reached, the run must be terminated as operation is no longer feasible.

Figure 3:
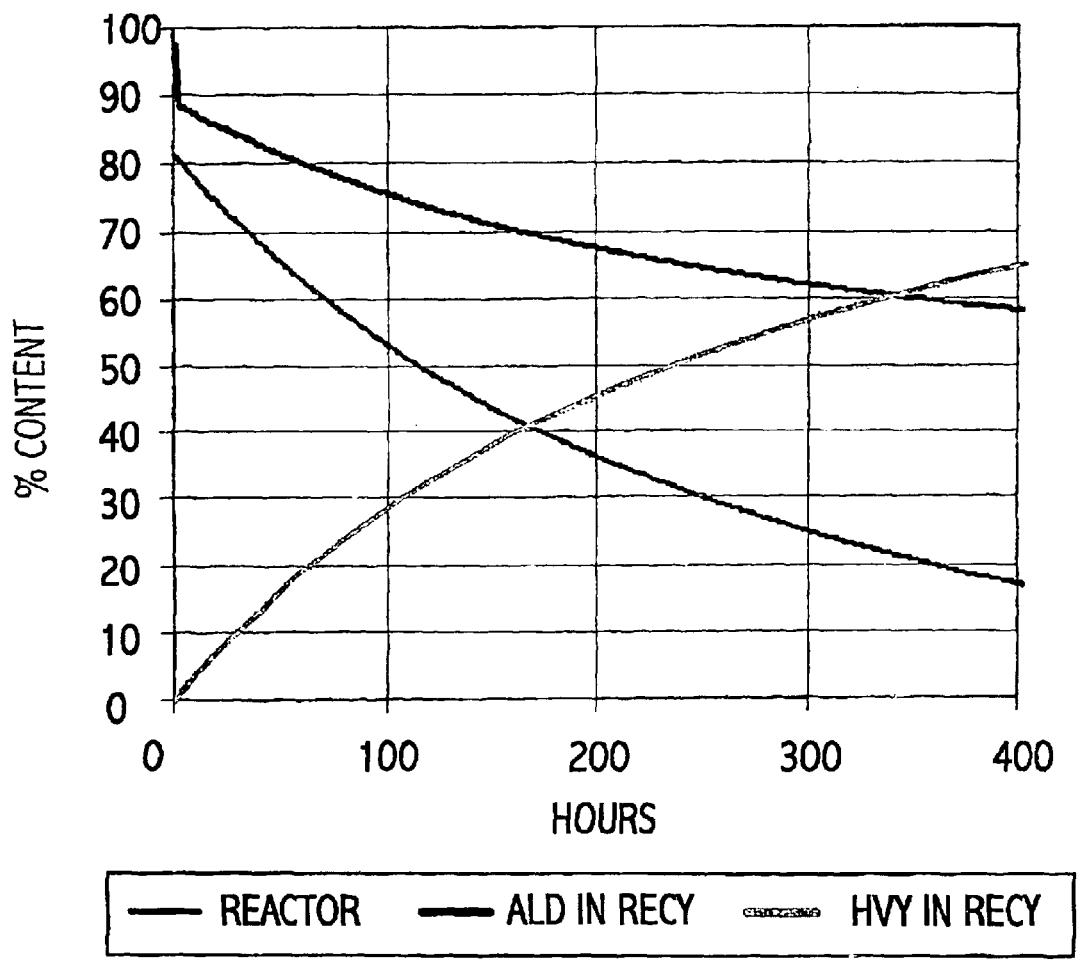
FIG. 3 is a graph of aldehyde, heavies and olefin content against time for Comparative Example 1.

FIG. 3 illustrates the performance of the reactor where no recycling of the rhodium is used and illustrates the decline of olefin conversion in the reactors and the build up of heavies. In this comparative example the heavies concentration exceeds 60 wt % at approximately 350 hours.

EXAMPLE 1

The reactor is again run at 110° C. but a purge equivalent to 0.2 wt % of the recycle flow is taken and treated to rhodium recovery as described in FIG. 2 and returned to the reactor.

Figure 4:
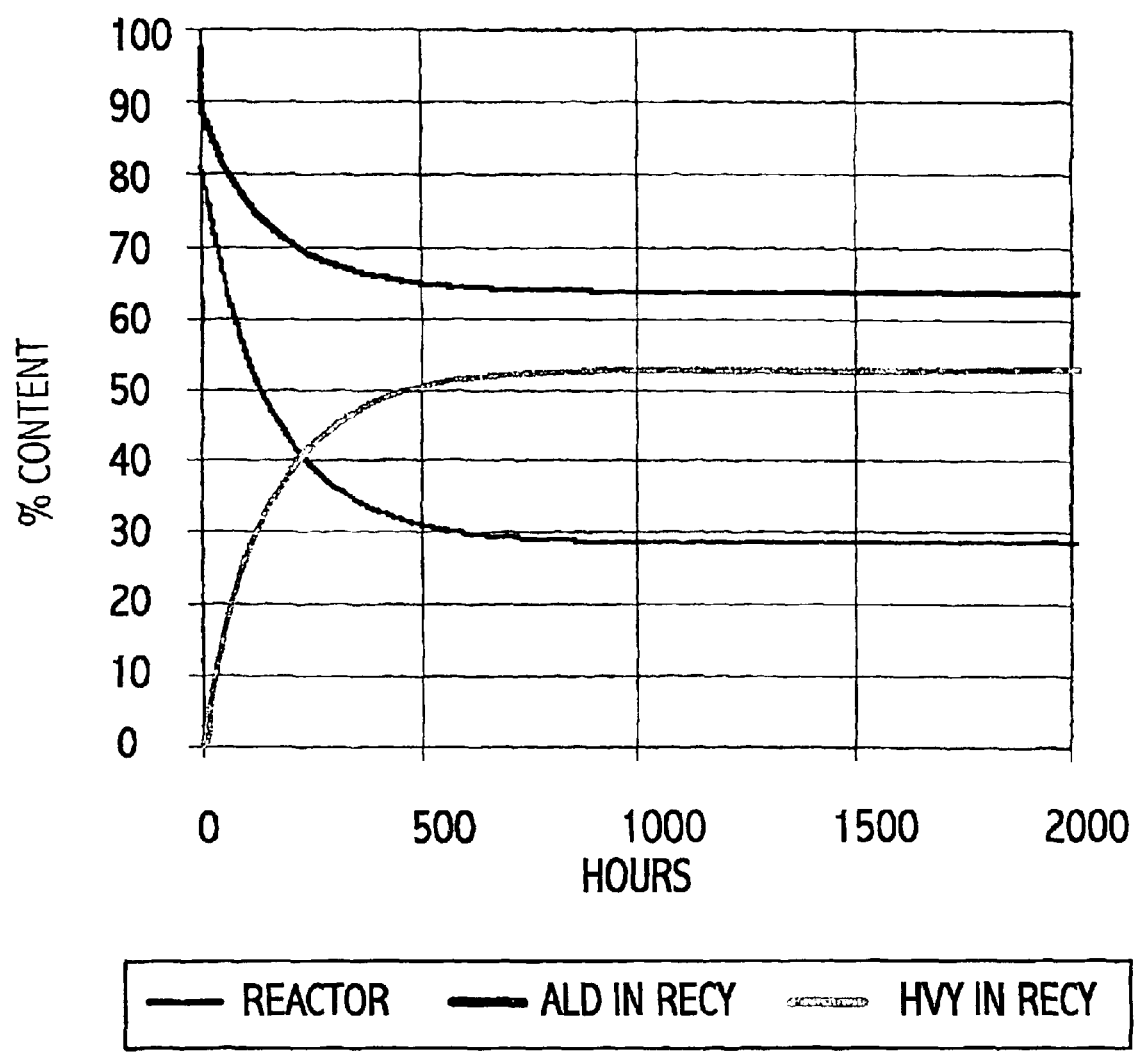
FIG. 4 is a graph of aldehyde, heavies and olefin content against time for Example 1.

FIG. 4 illustrates how the conversion of olefin and overall performance of the reactor reaches a steady state after approximately 1000 hours on-line with the heavies being controlled well below 60 wt % allowing the reactor to be run continuously at these conditions.

COMPARATIVE EXAMPLE 2

Figure 5:
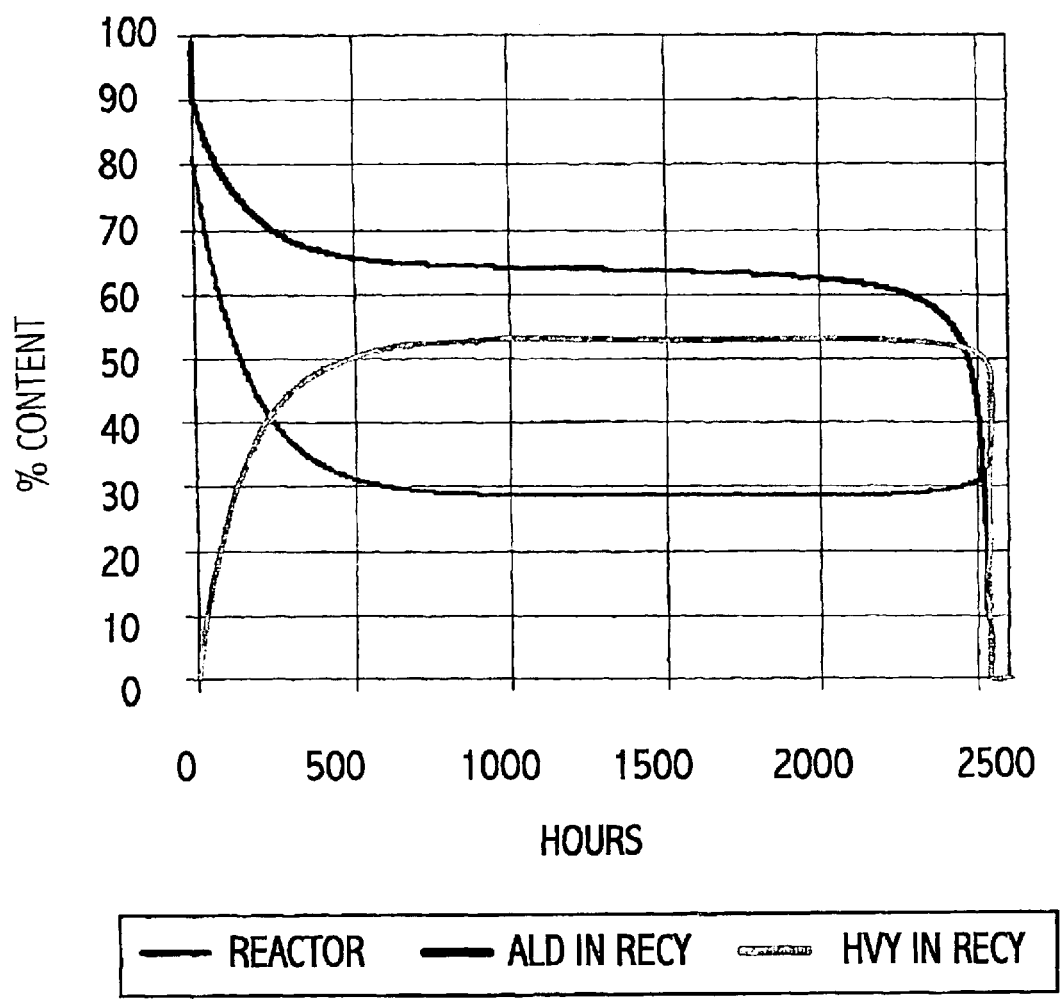
FIG. 5 is a graph of aldehyde, heavies and olefin content against time for Comparative Example 2.

Example 1 is repeated with the reactors running at a temperature of 110° C. and purge rate of 0.2% of the recycle flow. The reactor is started with a rhodium concentration of 500 ppm. The feed also contains a poison such that 1 liter of feed contains sufficient poison to react with approximately 1 mg of rhodium. The purge from the recycle stream is treated to recover the rhodium but the poison is not separated from the rhodium such that it is recycled to the reactor. As a consequence the heavies reaches a steady state level after 500 hours but the activity declines as the rhodium is deactivated. The productivity falls off dramatically at around 2500 hours as illustrated in FIG. 5.

EXAMPLE 2

Figure 6:
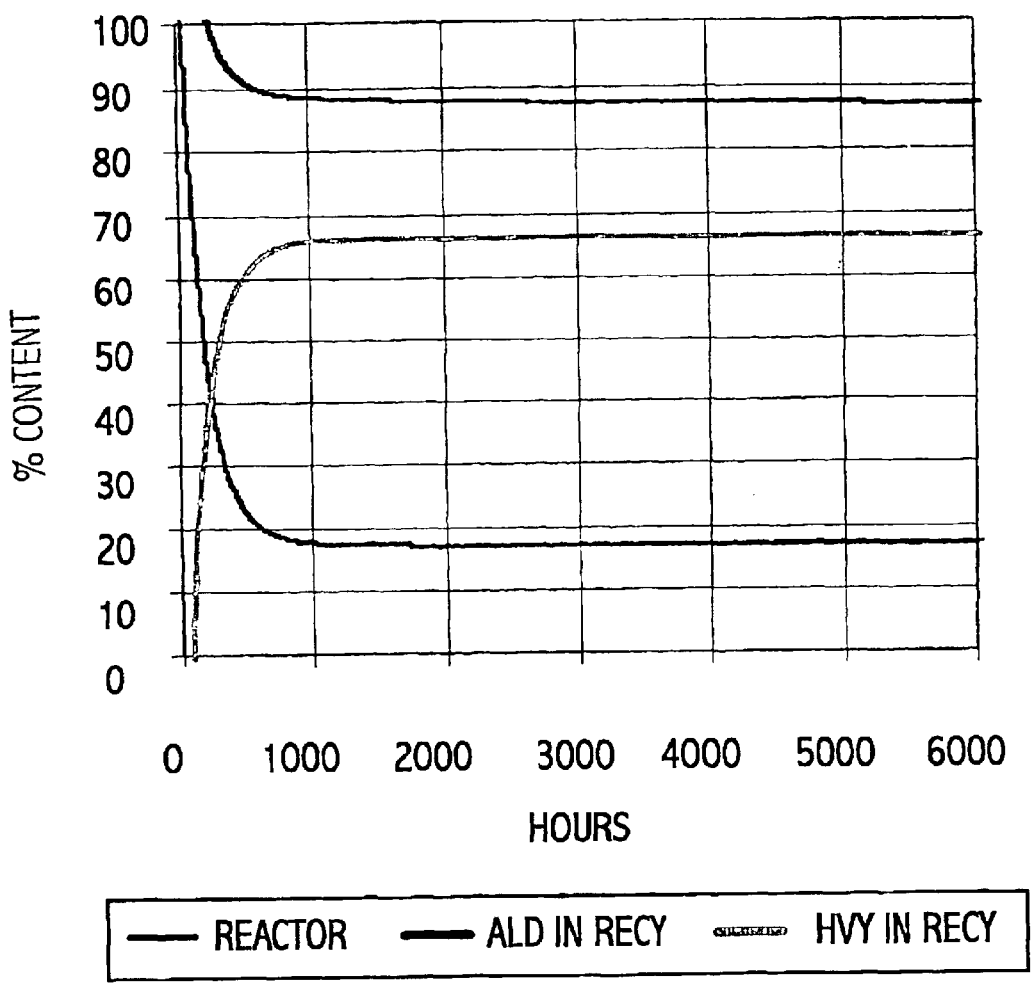
FIG. 6 is a graph of aldehyde, heavies and olefin content against time for Example 2.

Comparative Example 2 is repeated except that the poison in the purge is not reintroduced with the recovered rhodium. After 1000 hours the heavies concentration has reached steady state at approximately 50 wt %. The olefin conversion levels out but continues a small decline for a further 5000 hours. After 5000 hours steady state is achieved as illustrated in FIG. 6

COMPARATIVE EXAMPLE 3

Figure 7:
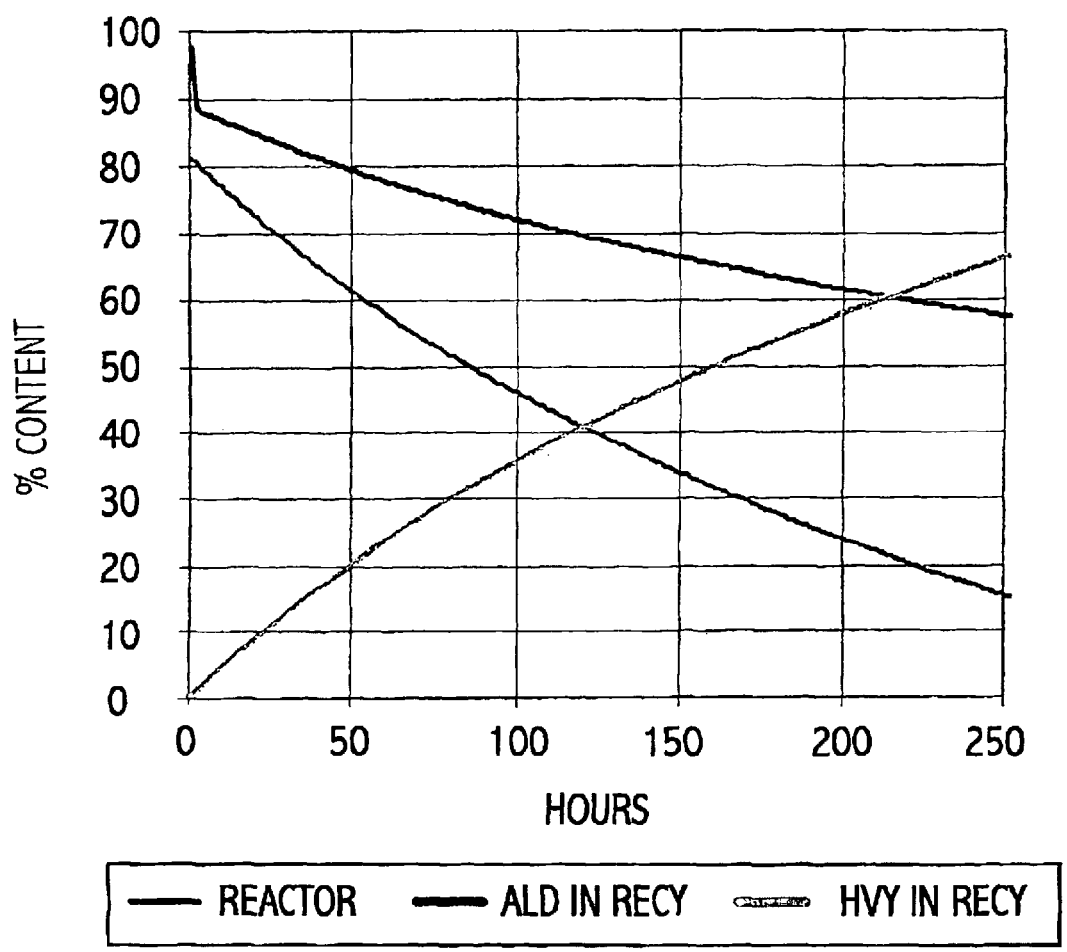
FIG. 7 is a graph of aldehyde, heavies and olefin content against time for Comparative Example 3.

Comparative Example 1 is repeated, however in addition to heavies forming as a result of aldol condensation reactions, the feed contains 0.1 wt % involatile material. As a result the level of heavies in the recycle increases more rapidly than shown in Comparative Example 1. In this example the maximum allowable heavies concentration is exceeded after only 200 hours as illustrated in FIG. 7.

EXAMPLE 3

Figure 8:
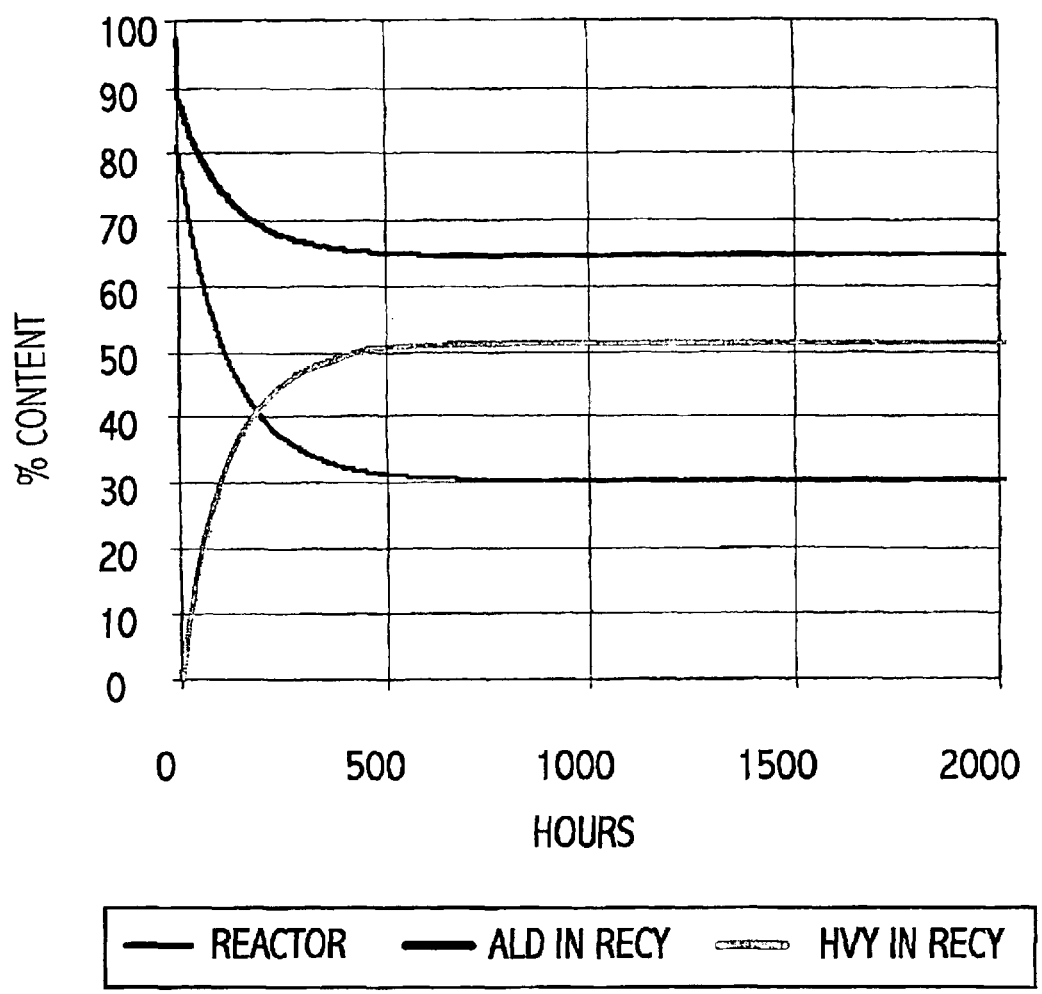
FIG. 8 is a graph of aldehyde, heavies and olefin content against time for Example 3.

Example 1 is repeated with a feed containing 0.1 wt % involatile material and an increased purge rate of 0.4 wt %. As illustrated in FIG. 8 the heavies in the recycle reaches a stable maximum of approximately 50 wt % after 1000 hours.

EXAMPLE 4

A solution of hexene (50 ml) in texanol (50 ml) was hydroformylated to extinction using a catalyst prepared from 0.1 mmol of Rhodium(acac)(CO)2 and 0.6 mmol of a bidentate phosphite of the formula (ArO)2P(OAr—ArO)P(OAr)2 where Ar represents various aryl functional groups. Amberlyst DPT-1 was then added to the autoclave (8 g, dry weight). After stirring at 65° C. for 1 hour the concentration of rhodium in solution had dropped to 25 ppm. The autoclave was then pressurised to 1000 psig with hydrogen and cooled to room temperature. After 18 hours the concentration of rhodium in solution had increased to 75 ppm.

What is claimed is:

1. A continuous hydroformylation process for the production of an aldehyde by hydroformylation of an olefin which comprises:
   (a) providing a hydroformylation zone containing a charge of a liquid reaction medium having dissolved therein a rhodium hydroformylation catalyst comprising rhodium in combination with carbon monoxide and a ligand;
   (b) supplying the olefin to the hydroformylation zone;
   (c) maintaining temperature and pressure conditions in the hydroformylation zone conducive to hydroformylation of the olefin;
   (d) recovering from the liquid hydroformylation medium a hydroformylation product comprising aldehyde;
   (e) recovering from the hydroformylation zone a stream comprising the rhodium catalyst;
   (f) contacting at least a portion of the stream with a solid acidic absorbent under process conditions which allow at least some of the rhodium to become bound to the absorbent;
   (g) subjecting the rhodium bound to the absorbent, under process conditions which allow desorption of the metal, to a fluid stripping medium comprising hydrogen and solvent;
   (h) recovering the rhodium hydride catalyst; and
   (i) recycling the rhodium hydride catalyst to the hydroformylation zone.

2. A process according to claim 1 wherein the stream from step (e) is divided and a first part is recycled to the hydroformylation zone and a second part is subjected to steps (f) to (i).

3. A process according to claim 2 wherein the second part is at least about 0.01% of the stream from step (e).

4. A process according to claim 1 wherein the olefin is one of more olefin selected from $C_2$ to $C_{20}$ olefins.

5. A process according to claim 1 wherein the olefin is not subjected to pretreatment before being charged to the hydroformylation zone.

6. A process according to claim 1 wherein the rhodium hydride catalyst is a rhodium carbonyl complex comprising rhodium in complex combination with triphenylphosphine.

7. A process according to claim 1 wherein the hydroformylation zone is operated at a temperature which will cause thermal deactivation of the catalyst.

8. A process according to claim 1 wherein the hydroformylation zone is operated at a temperature of from about 40° C. to about 180° C.

9. A process according to claim 1 wherein the feed to the hydroformylation zone includes poisons, inhibitors or poisons and inhibitors.

10. A process according to claim 9 wherein the hydroformylation zone includes at least 0.5 gram equivalent of rhodium of poisons, inhibitors or poisons and inhibitors per cubic meter of feed.

11. A process according to claim 1 wherein the feed to the hydroformylation zone includes heavies or compounds likely to form heavies in the hydroformylation zone or both.

12. A process according to claim 1 wherein the fluid stripping medium is a single fluid phase.

13. A process according to claim 12 wherein the single fluid phase is a supercritical phase.

14. A process according to claim 12 wherein the fluid stripping medium comprises two fluid phases.

15. A process according to claim 1 wherein the stream collected in step (e) contains non-volatile by-products of the reaction.

16. A process according to claim 1 wherein the stream having been contacted with the solid acidic absorbent is removed.

17. A process according to claim 1 wherein the acidic absorbent is an ion-exchange resin.

18. A process according to claim 1 wherein the acidic absorbent is a styrene divinyl copolymer containing sulphonic acid groups or carboxylic acid groups.

19. A process according to claim 1 wherein the acidic absorbent has a silica-containing backbone and an acidic functional group attached to the silica.

20. A process according to claim 19 wherein the acidic functional group is an aromatic carboxylic acid, an aliphatic carboxylic acid, an aromatic sulphonic acid or an aliphatic sulphonic acid.

21. A process according to claim 1 wherein step (g) is carried out at a temperature of from about 20° C. to about 100° C.

22. A process according to claim 21 wherein the temperature is in the region of about 50° C. to about 95° C.

23. A process according to claim 1 wherein the stream recovered in step (e) is concentrated prior to contact with the acidic absorbent.

24. A process according to claim 1 wherein the stream recovered in step (e) is diluted with a solvent compatible with the absorbent before it is contacted with the absorbent.

25. A process according to claim 1 wherein the stream recovered in step (e) is subjected to oxidation to break clustered catalyst prior to being contacted with the acidic absorbent.

26. A process according to claim 25 wherein the stream having been subjected to oxidation is treated to hydrocarbonylation.

27. A process according to claim 1 wherein the gaseous phase of the stripping medium additionally includes carbon monoxide.

* * * * *